United States Patent
Komata et al.

(12) 
(10) Patent No.: US 6,395,940 B1
(45) Date of Patent: May 28, 2002

(54) METHOD FOR PRODUCING PERHALOGENATED CYCLOPENTENE

(75) Inventors: Takeo Komata, Saitama; Takayuki Nishimiya, Yamaguchi; Fuyuhiko Sakyu, Saitama; Hideaki Imura, Saitama; Mikio Ujiie, Saitama; Masatomi Kanai, Saitama, all of (JP)

(73) Assignees: Central Glass Company, Limited, Ubs; Nippon Zeon Co., Ltd., Tokyo, both of (JP)

( * ) Notice: Subject to any disclaimer, the term of this patent is extended or adjusted under 35 U.S.C. 154(b) by 0 days.

(21) Appl. No.: 09/486,608
(22) PCT Filed: Sep. 17, 1998
(86) PCT No.: PCT/JP98/04175
§ 371 (c)(1),
(2), (4) Date: Mar. 1, 2000
(87) PCT Pub. No.: WO99/14173
PCT Pub. Date: Mar. 25, 1999

(30) Foreign Application Priority Data

Sep. 19, 1997 (JP) ............................................... 9-252222
Jul. 9, 1998 (JP) ............................................ 10-194140

(51) Int. Cl.$^7$ ................................................ C07C 17/20
(52) U.S. Cl. ........................................................ 570/160
(58) Field of Search ........................................ 570/160

(56) References Cited

U.S. PATENT DOCUMENTS

| | | |
|---|---|---|
| 2,449,233 A | 9/1948 | Kischitz |
| 2,459,783 A | 1/1949 | McBee |
| 3,178,482 A | 4/1965 | Baranauckas |
| 3,258,500 A | 6/1966 | Swamer |
| 3,381,044 A | 4/1968 | Wiedemann |
| 3,514,253 A | 5/1970 | Robota |
| 3,567,788 A | 3/1971 | Carr |
| 3,859,372 A | 1/1975 | Robota |

FOREIGN PATENT DOCUMENTS

| | | |
|---|---|---|
| DE | 39 35 493 | 5/1991 |
| EP | 055 659 | 7/1982 |
| EP | 366 797 | 5/1990 |
| JP | 8-333285 | 12/1996 |

OTHER PUBLICATIONS

Newcomer et al. (1949) "The Chemical Behavior of Hexachlorocyclopentadiene. I. Transformation to Octachloro–3a,4,7,7a–Tetrahydro–4, 7–methanoindene–1, 8–dione" *J. Amer. Chem. Soc.* 71: 946–951.

Henne et al., (1945) "Fluorinated Derivatives of Cyclopentene and Cyclopentane" *J. Amer. Chem. Soc.* 67:1235–1237.

XP–002090916, Derwent Database Abstract of JP 9–095458, Apr. 8, 1997.

*Primary Examiner*—Alan Siegel
(74) *Attorney, Agent, or Firm*—Crowell & Moring LLP

(57) ABSTRACT

The invention relates to a method for producing a first perhalogenated cyclopentene represented by the general formula: $C_5Cl_BF_{8-B}$ where B is an integer of from 0 to 7. The method includes a step of (a) fluorinating a second perhalogenated cyclopentene by hydrogen fluoride in a gas phase in the presence of a fluorination catalyst. The second perhalogenated cyclopentene is represented by general formula: $C_5Cl_AF_{8-A}$ where A is an integer of from 1 to 8, and A is not smaller than B. With this method, the first perhalogenated cyclopentene (e.g., 1,2-dichloro-3,3,4,4,5,5-hexafluorocyclopentene, another chlorofluorinated cyclopentene, or octafluorocyclopentene) can continuously easily be produced, for example, from octachlorocyclopentene obtained by chlorination of hexachlorocyclopentadiene that is easily available. Therefore, the above method is very useful as an industrial scale production method. In case that the first perhalogenated cyclopentene is octafluorocyclopentene, the method may further include a step of (b) fluorinating a reaction product of the step (a) in a way that is different from that of the step (a), thereby to convert said reaction product of the step (a) into octafluoropentene. The step (a) may be conducted by a multistep reaction wherein there are provided "m" of reaction zones in number where m is an integer of from 2 to 10. In this case, the reaction zones are arranged in series and such that a reaction temperature of each reaction zone is independently controllable.

12 Claims, No Drawings

METHOD FOR PRODUCING PERHALOGENATED CYCLOPENTENE

This application is a 371 of PCT/JP98/04175 filed Sep. 17, 1998.

BACKGROUND OF THE INVENTION

The present invention relates to methods for producing chlorofluorocyclopentenes and octafluorocyclopentene, which are useful as intermediates for 1,2,3,3,4,4,5,5-octafluorocyclopentane, which is useful as a fluorine-containing detergent, a fluorine-containing drying solvent, or the like, and as intermediates for various fluorine-containing compounds.

It is known that fluorinated cyclopentanes are produced at first by fluorinating chlorinated cycloalkenes corresponding to the fluorinated cyclopentanes to obtain vicinally chlorinated fluorocyclopentene derivatives, and then by fluorinating and hydrogenating these derivatives. It is known that vicinally chlorinated fluorocyclopentene derivatives are produced by a first method, in which perchlorocycloolefins are used, or a second method, in which perchloro cycloconjugated dienes are used. As an example of the first method, J. Am. Chem. Soc., 67, 1235 (1945) discloses a method for producing 1,2-dichlorohexafluorocyclopentene by reacting octachlorocyclopentene with a mixture of antimony trifluoride and antimony trifluorodichloride. Furthermore, German Patent No. 3935493 discloses a method for producing 1,2-dichlorohexafluorocyclopentene by reacting octachlorocyclopentene with chlorine and hydrogen fluoride in the presence of antimony pentachloride. As an example of the second method, Japanese Patent First Publication JP-A-8-333285 discloses a method for producing 1,2-dichloro-3,3,4,4,5,5-hexafluorocyclopentene at first by reacting hexachlorocyclopentadiene with chlorine in the presence of antimony trichloride, thereby to respectively convert the hexachlorocyclopentadiene and antimony trichloride to octachlorocyclopentene and antimony pentachloride, and then by adding hydrogen fluoride thereto. On the other hand, U.S. Pat. No. 2,459,783 discloses a method for producing 1,2-dichlorohexafluorocyclopentene by reacting hexachlorocyclopentene with antimony pentafluoride. U.S. Pat. No. 2,449,233 discloses a method for producing 1,2-dichlorohexafluorocyclopentene by reacting hexachlorocyclopentadiene with hydrogen fluoride in the presence of antimony pentachloride.

In each of the above-mentioned conventional methods, a liquid phase reaction in the presence of an antimony halide catalyst is used. Thus, corrosiveness of the antimony halide may cause problems. Furthermore, in case that hydrogen fluoride is used as a fluorination-agent in an industrial scale production, the reaction pressure may become as high as 10–30 kg/cm². This may cause some limitations in the selection of devices.

SUMMARY OF THE INVENTION

It is an object of the present invention to provide a method for producing a perhalogenated cyclopentene, particularly octafluorocyclopentene, which method is appropriate for the production of the same in an industrial scale.

According to the present invention, there is provided a method for producing a first perhalogenated cyclopentene represented by the general formula $C_5Cl_BF_{8-B}$ where B is an integer of from 0 to 7. The method comprises a step of (a) fluorinating a second perhalogenated cyclopentene by hydrogen fluoride in a gas phase in the presence of a fluorination catalyst. The second perhalogenated cyclopentene is represented by the general formula $C_5Cl_AF_{8-A}$ where A is an integer of from 1 to 8, and A is not smaller than B. With this method, the first perhalogenated cyclopentene (e.g., 1,2-dichloro-3,3,4,4,5,5-hexafluorocyclopentene, another chlorofluorinated cyclopentene, or octafluorocyclopentene) can continuously easily be produced, for example, from octachlorocyclopentene obtained by chlorination of hexachlorocyclopentadiene that is easily available. Therefore, the above method is very useful as an industrial scale production method.

According to the present invention, in case that the first 1o perhalogenated cyclopentene is octafluorocyclopentene, the above method may further comprise a step of (b) fluorinating a reaction product of the step (a) in a way that is different from that of the step (a), thereby to convert the reaction product of the step (a) into octafluoropentene. The reaction product of the step (a) is a perhalogenated cyclopentene represented by the general formula $C_5Cl_BF_{8-B}$ where B is an integer of from 0 to 7 or the general formula $C_5Cl_AF_{8-A}$ where A is an integer of from 1 to 8, and A is not smaller than B.

According to the present invention, the above step (a) may be conducted by a multistep reaction wherein there are provided "m" of reaction zones in number where m is an integer of from 2 to 10. The reaction zones are arranged in series and such that a reaction temperature of each reaction zone is independently controllable. With this multistep reaction, it becomes possible to decrease the production of tarry substances and thus maintain the fluorination catalyst in lifetime. Therefore, it becomes possible to produce the first perhalogenated cyclopentene continuously for a long time without interrupting the operation.

DESCRIPTION OF THE PREFERRED EMBODIMENTS

In the invention, 1,2-dichloro-3,3,4,4,5,5-hexafluorocyclopentene-1 is 1,2-dichlorohexafluorocyclopentene or 1,2-dichloro-3,3,4,4,5,5-hexafluorocyclopentene. Hereinafter, unless otherwise described, octachlorocyclopentene used as the raw material of the method of the invention may be replaced with a chlorofluorocyclopentene obtained by partially fluorinating octachlorocyclopentene. Furthermore, "1,2-dichlorohexafluorocyclopentene" as the reaction product may include other chlorofluorocyclopentenes, chloroheptafluorocyclopentene, and octafluorocyclopentene.

As stated above, the first perhalogenated cyclopentene, the aimed product of the invention, is represented by the general formula $C_5Cl_BF_{8-B}$ where B is an integer of from 0 to 7. In other words, the number of chlorine atoms of this cyclopentene is an integer of 0–7, and the number of fluorine atoms thereof is an integer of 1–8, and the total of the number of chlorine atoms and that of fluorine atoms is 8. In this cyclopentene, the halogen atom may be bonded to any carbon atom. The first perhalogenated-cyclopentene is not particularly limited, and its nonlimitative examples are octafluorocyclopentene, 1-chloro-heptafluorocyclopentene, 1,2-dichloro-3,3,4,4,5,5-hexafluorocyclopentene, 1,2,4-trichloro-3,3,4,5,5-pentafluorocyclopentene, 1,2,3,4-tetrachloro-3,4,5,5-tetrafluorocyclopentene, 1,2,3,4,4-pentachloro-3,5,5-trifluorocyclopentene, hexachloro-3,3-difluorocyclopentene, hexachloro-4,4-difluorocyclopentene, and heptachloro-5-fluorocyclopentene.

As stated above, the second perhalogenated cyclopentene, the raw material of the invention, is represented by the general formula $C_5Cl_AF_{8-A}$ where A is an integer of from 1 to 8. In other words, the number of chlorine atoms of this cyclopentene is an integer of 1–8, and the number of fluorine atoms thereof is an integer of 0–7, and the total of the number of chlorine atoms and that of fluorine atoms is 8. In this cyclopentene, the halogen atom may be bonded to any carbon atom. The second perhalogenated cyclopentene is not particularly limited, and its nonlimitative examples are 1-chloro-heptafluorocyclopentene, 1,2-dichloro-3,3,4,4,5,5-hexafluorocyclopentene, 1,2,4-trichloro-3,3,4,5,5-pentafluorocyclopentene, 1,2,3,4-tetrachloro-3,4,5,5-tetrafluorocyclopentene, 1,2,3,4,4-pentachloro-3,5,5-trifluorocyclopentene, hexachloro-3,3-difluorocyclopentene, hexachloro-4,4-difluorocyclopentene, heptachloro-5-fluorocyclopentene, and octachlorocyclopentene.

The first or second perhalogenated cyclopentene of the invention can be synthesized by a conventional method. For example, Newcomer; McBee, J. Amer. Chem. Soc., 71<1949>946, 950 discloses a method for producing octachlorocyclopentene by chlorinating hexachlorocyclopentadiene by chlorine in the presence of a catalyst (e.g., metal chloride). Furthermore, Henne et al., J. Am. Chem. Soc., 67, 1235 (1945) discloses a reaction of octachlorocyclopentene with a mixture of antimony trifluoride and antimony trifluorodichloride, thereby to produce 1,2-dichlorohexafluorocyclopentene, 1,2,4-trichloro-3,3,4,5,5-pentafluorocyclopentene and 1,2,3,4-tetrachloro-3,4,5,5-tetrafluorocyclopentene.

In the invention, it is preferable that the fluorination catalyst comprises at least one metal selected from metals of 4, 5, 6, 7, 8, 9, 10, 11, 12, 13, 14, and 15 groups of periodic table. These metals are preferably chromium, manganese, cobalt, nickel, iron, molybdenum, niobium, aluminum, zinc, copper, antimony, titanium, tin, and tantalum. Of these, chromium and antimony can particularly preferably be used. In case that at least two metals are used for the fluorination catalyst, one of the at least two metals is preferably chromium or antimony. Furthermore, the fluorination catalyst may be at least one selected from the group consisting of metal oxides, metal fluorides (fluorinated metals), metal chlorides (chlorinated metals), metal fluorochlorides (fluorochlorinated metals), metal oxyfluorides (partially fluorinated metal oxides), metal oxychlorides (partially chlorinated metal oxides), and metal oxyfluorochlorides (partially fluorochlorinated metal oxides). The at least one metal used for the fluorination catalyst may be carried on a conventional carrier. The carrier of the fluorination catalyst is not particularly limited, as long as it is stable in the fluorination of the invention. Examples of the carrier are activated carbon, metallic aluminum, zirconia, magnesia, titania, modified clays prepared by removing silica therefrom, for example, with hydrogen fluoride, aluminum oxide (alumina), aluminum fluoride, aluminum chloride, aluminum fluorochloride, aluminum oxyfluoride (partially fluorinated alumina), aluminum oxychloride, and aluminum oxyfluorochloride. Particularly preferable examples of the fluorination catalyst are chromium-carried activated carbon, chromium-carried alumina, activated carbon carrying thereon chromium oxide, activated carbon carrying thereon partially fluorinated chromium oxide, and antimony-carried activated carbon.

In the invention, the activated carbon, which is used as a carrier of the fluorination catalyst, is not limited to a particular type. The activated carbon may be prepared from a vegetable raw material such as wood, sawdust, charcoal, coconut husk coal, palm core coal, or raw ash; a coal such as peat, lignite, brown coal, bituminous coal, or anthracite; a petroleum raw material such as petroleum residue, sulfuric sludge, or oil carbon; or a synthetic resin raw material. The activated carbon may be selected from various commercial activated carbons. Examples of commercial activated carbons that are usable in the invention are an activated carbon having a trade name of CALGON GRANULAR ACTIVATED CARBON CAL that is made of bituminous coal and made by TOYO CALGON CO. and a coconut husk coal made by Takeda Chemical Industries, Ltd. An activated carbon used in the invention is generally in the form of granules. Its shape and size are not particularly limited, and may be decided depending on the reactor's size. It is preferable that the activated carbon used in the invention has a large specific surface area. Commercial products of activated carbon will suffice for the invention with respect to specific surface area and micropore volume. In the invention, the specific surface area of the activated carbon is preferably greater than 400 m$^2$/g, more preferably from 800 to 3,000 m$^2$/g. Furthermore, the micropore volume of the activated carbon is preferably greater than 0.1 cm$^3$/g, more preferably from 0.2 to 1.0 cm$^3$/g. In case that activated carbon is used as a carrier in the invention, it is preferable to activate the surface of the carrier and remove ashes therefrom by immersing the activated carbon in a basic aqueous solution of ammonium hydroxide, sodium hydroxide, potassium hydroxide or the like at about room temperature for about 10 hr or more or by subjecting the activated carbon to a pretreatment with an acid such as nitric acid, hydrochloric acid or hydrofluoric acid at room temperature or under a heated condition. This pretreatment is conventionally used, upon the use of activated carbon as a catalyst carrier.

In the invention, it is preferable to remove water as much as possible from the carrier by heating, vacuum or the like, prior to the application of a high valency metal halide in order to prevent deterioration of the halide caused by hydrolysis or the like. The metal of this halide is selected from antimony, titanium, tin, tantalum and the like, In the invention, alumina used as the carrier of the fluorination catalyst is not limited to a particular type. It is possible to use an alumina prepared by forming a precipitate from an aluminum salt aqueous solution by using a basic substance such as ammonia and then by molding and desiccating the precipitate. In fact, it is preferable to use γ-alumina that is commercially available for use as a catalyst carrier or desiccant.

In the invention, the amount of at least one metal that is carried on a carrier is preferably from 0.1 to 50 parts by weight, more preferably from 0.5 to 50 parts by weight, still more preferably from 2 to 50 parts by weight, further more preferably from 5 to 50 parts by weight, relative to 100 parts by weight of the carrier. As the amount of the at least one metal increases, the catalyst becomes more active. However, if its amount is too much, the catalyst may become powdery and thus should be handled with care.

In the invention, the method for preparing the fluorination catalyst is not particularly limited. The carrier of the fluorination catalyst may be, for example, an aluminum oxide, such as γ-alumina, or a partially fluorinated alumina that has been treated by hydrogen fluoride, hydrogen chloride, chlorofluorohydrocarbon or the like, or activated carbon. In the preparation of the fluorination catalyst, the carrier may be immersed into a solution of the at least one compound or the at least one compound itself, if it is in the form of liquid, or alternatively the solution or the at least one compound itself may be sprayed on the carrier. Then, the carrier is dried and then brought into contact with a fluorination agent in the gas form (e.g., hydrogen fluoride and chlorofluorohydrocarbon) under a heated condition, thereby to partially or completely fluorinate the carrier or the at least one compound carried thereon. With this, the preparation of the fluorination catalyst is completed. In case that a fluorinated alumina is used as the carrier, it is preferable in the preparation of the fluorination catalyst to bring the carrier into contact with hydrogen fluoride at a temperature (preferably of about 150–800° C.) that is not lower than that of the fluorination of the second perhalogenated cyclopentene. With this, the fluorine content of the fluorination catalyst will be stable during a reaction period. In contrast with the above, when the at least one compound is not carried on a carrier, the at least one compound may be prepared, as follows. At first, a metal hydroxide is precipitated from a solution of a compound of the at least one metal, using a basic substance such as ammonia. After that, this metal hydroxide is turned into a metal oxide, for example, by sintering, and then this metal oxide is partially or completely modified by halogen, using hydrogen fluoride, hydrogen chloride, chlorofluorohydrocarbon, or the like. For example, the metal oxide may be prepared by sintering a chromia gel that was precipitated from a chromium nitrate aqueous solution by using an ammonia aqueous solution. Furthermore, the metal oxide may be prepared by kneading the chromia gel with an alumina gel obtained by a similar manner as that of the chromia gel and then by sintering the kneaded mixture. Still furthermore, the metal oxide may be prepared by sintering a mixed gel obtained by coprecipitation from a chromium nitrate aqueous solution in which the at least one metal (e.g., manganese) used for the fluorination catalyst is dissolved. It is needless to say that the metal oxide can similarly be prepared by using another metal.

In the invention, it is optional to add an additive that is at least one element of alkali-earth metals such as Mg and Ca and lanthanide series elements such as La and Ce, to the fluorination catalyst. This additive prevents recrystallization of an oxyhalide used as the at least one metal or as the carrier, thereby maintaining activity of the first fluorination catalyst. Weight ratio of the at least one metal to the additive is preferably from 50:50 to 99.9:0.1 and more preferably from 70:30 to 99:1.

In the invention, at least one metal compound used for preparing the fluorination catalyst may be at least one of nitrate, chloride, organic acid salt, organic complex and the like of the at least one metal, which is soluble in a solvent such as water, ethanol, or acetone. Furthermore, the at least one metal compound, such as oxide and hydroxide, or the elemental metal may be dissolved in a mineral acid, such as hydrochloric acid and nitric acid, in the preparation of the fluorination catalyst. Nonlimitative examples of the at least one metal compound are chromium nitrate, chromium trichloride, chromium trioxide, potassium dichromate, manganese nitrate, manganese chloride, manganese dioxide, manganese acetate, nickel nitrate, nickel chloride, nickel acetate, cobalt nitrate, cobalt chloride, iron nitrate, iron chloride, molybdenum chloride, niobium chloride, aluminum nitrate, aluminum chloride, zinc chloride, copper nitrate, copper chloride, antimony trichloride, antimony pentachloride, antimony pentafluoride, titanium tetrachloride, titanium trichloride, tin tetrachloride, and tantalum pentachloride.

In the invention, a fluorination catalyst having a carrier (e.g., activated carbon) carrying thereon a halide of a metal of high valence, such as antimony, titanium, tin and tantalum, can be prepared as follows. For example, such halide itself, if it is in the form of liquid at room temperature, is gradually added to an activated carbon that has been subjected, according to need, to a pretreatment such as desiccation, acid treatment and the like. Alternatively, the activated carbon is immersed in a solution, in which such halide is dissolved in an inert solvent, followed by heating and/or vacuum. Examples of this inert solvent are chlorinated solvents such as carbon tetrachloride, chloroform, methylene chloride, tetrachloroethylene, trichloroethylene, and tetrachloroethane; fluorochlorinated solvents such as 2,2-dichloro-1,1,1-trifluoroethane, 1,1,-dichloro-1-fluoroethane, 3,3-dichloro-1,1,1,2,2-pentafluoropropane, and 1,3-dichloro-1,1,2,2,3-pentafluoropropane; and alcohols such as methanol, ethanol and isopropanol. Antimony compounds are relatively easily oxidized. Thus, it is optional to immerse a carrier in a solution, in which a halide of a metal of low valence, such as antimony trichloride, is dissolved in the above-mentioned inert solvent, and then turn this halide into a pentavalent halide, for example, by chlorine. In this case, such halide is assumed to serve as a catalyst, while its high valence is maintained. Thus, as mentioned hereinafter, such halide may have a catalytic activity at a relatively low temperature. In the invention, a halide of lo high valence metal may be antimony pentachloride, antimony pentafluoride, tin tetrachloride, titanium tetrachloride, or tantalum pentachloride. The carrier for this halide may be activated carbon. This halide may be a mixture of at least two halides. In fact, it is preferable to add to antimony pentachloride a small amount of tin pentachloride, titanium tetrachloride, tantalum pentachloride, or a chloride of a metal selected from chromium, manganese, cobalt, nickel, iron, molybdenum, niobium, aluminum, zinc and copper. The active species of catalyst may not be certain, but is assumed to be a mixed halide in which chlorine has partially been replaced with fluorine.

In the invention, compositional change of the fluorination catalyst during the fluorination (i.e., the above step (a)) can effectively be prevented by treating, prior to the fluorination, the fluorination catalyst with a fluorination agent such as hydrogen fluoride, fluorohydrocarbon or fluorochlorohydrocarbon, at a temperature not lower than the reaction temperature of the fluorination. Once the fluorination catalyst activity is inactivated by the reaction, it is possible to reactivate the catalyst by bringing the inactivated catalyst into contact with an oxidative substance such as oxygen, air, ozone and chlorine. In some cases, it is preferable to continuously or intermittently supply to the reaction system an active substance, such as oxygen, ozone, chlorine, chlorine fluoride, chlorine trifluoride, nitrogen oxide, and nitrous oxide, in order to maintain the fluorination catalyst in lifetime.

In the invention, the reaction temperature of the fluorination of the second perhalogenated cyclopentene is preferably from 40 to 800° C., and it varies depending on the type and preparation method of the metal of the fluorination catalyst. For example, even if the catalyst metal is chromium, manganese, cobalt, nickel, iron, molybdenum, niobium, aluminum, zinc, copper or the like, or antimony, titanium, tin, tantalum or the like, the reaction temperature is preferably from about 150 to about 800° C., more preferably from 200 to 750° C., still more preferably from 250 to 700° C., in case that the fluorination catalyst contains as an active species such metal, which is under a condition of low valence. On the other hand, in case that the fluorination catalyst contains as an active species a halide of a metal of high valence, such as antimony, titanium, tin, tantalum and the like, the reaction temperature is preferably from about 40 to about 300° C., more preferably from 50 to 250° C., still more preferably from 60 to 200° C. If the reaction temperature is lower than the lower limit (150 or 40° C.), the reaction rate may become too low and thus impractical. If the reaction temperature is too high, the reaction rate becomes high. However, the fluorination catalyst may be deteriorated, and it is not economical, since it requires a large amount of heat energy.

In the invention, the molar ratio of the second perhalogenated cyclopentene, which is supplied to the reaction zone, to hydrogen fluoride varies, depending on the particular types of the first and second perhalogenated cyclopentenes and the reaction temperature. For example, if it is intended to obtain 1,2-dichloro-3,3,4,4,5,5-hexafluorocyclopentene from octachlorocyclopentene, the molar ratio (the second perhalogenated cyclopentene/ hydrogen fluoride) is preferably from 1/60 to 1/6, more preferably from 1/50 to 1/8, still more preferably from 1/40 to 1/10. It is preferable to suitably reduce the amount of hydrogen fluoride relative to that of the second perhalogenated cyclopentene, in case that the second perhalogenated cyclopentene is in a partially fluorinated form or that the first perhalogenated cyclopentene is intended to have a lower degree of fluorination. If the amount of hydrogen fluoride is excessive, the production per unit time may become too low. On the other hand, if it is too small, conversion and yield may become too low.

In the invention, the reaction pressure of the fluorination is not particularly limited. It is preferably from 1 to 10 kg/cm$^2$ in view of the selection of devices. It is preferable to choose a suitable reaction condition in which intermediate substances and hydrogen fluoride, which are present in the reaction system, do not essentially liquefy, that is, they are not present in the form of liquid drops. The contact time of the fluorination is preferably from 0.1 to 300 seconds, more preferably from 1 to 100 seconds, still more preferably from 5 to 50 seconds.

In the invention, a reactor used in the fluorination is preferably made of a material that is heat resistant and corrosion resistant against hydrogen fluoride, hydrogen chloride and the like, such as stainless steel, Hastelloy, Monel metal or platinum, or a material lined with one of these metals. In the invention, the reaction products (the first perhalogenated cyclopentene) may be purified by a conventional purification process that is not particularly limited. In this process, for example, the reaction products, together with hydrogen chloride and the unreacted hydrogen fluoride, are taken out of the reactor in the form of gas or liquid. Then, they are washed with water and/or a basic solution or subjected to a treatment such as distillation or liquid phase separation, to remove hydrogen chloride and an excessive amount of hydrogen fluoride. Then, the remaining acid substances are removed by a basic substance or the like, followed by rectification, thereby to obtain the first perhalogenated cyclopentene.

As stated above, after the step (a), it is optional to conduct a step of (b) fluorinating a reaction product of the step (a) in a way that is different from that of the step (a). If the step (b) is conducted after the step (a), the above-mentioned rectification is not necessarily needed, depending on the method of fluorination of the step (a). In fact, in some cases, it may be only necessary between the steps (a) and (b) to remove acid substances from the reaction products. In other cases, even the removal of acid substances therefrom may not be necessary, but only the decrease of the acid content of the reaction products may be sufficient. For example, the step (b) can be a fluorination in which chlorine atom of the reaction products of the step (a) is replaced with fluorine atom of a metal fluoride. This metal fluoride is commonly used for fluorinating chlorinated alkanes and chlorinated alkenes. In the step (b), a mixture of first perhalogenated cyclopentenes can be fluorinated. The metal fluoride used in the step (b) is not particularly limited, and may be an alkali metal fluoride, such as lithium fluoride, sodium fluoride, potassium fluoride, cesium fluoride and rubidium fluoride. Of these, potassium fluoride and cesium fluoride are preferable. The amount by mol of this metal fluoride is preferably at least B, more preferably from B to 10B, still more preferably from B to 5B, relative to 1 mol of the raw material of the step (b), that is, the first perhalogenated cyclopropene represented by the general formula $C_5Cl_BF_{8-B}$ where B is an integer of from 0 to 7. According to need, it is optional to use a solvent in the step (b). Examples of this solvent are acid amides such as formamide, acetamide, N,N-dimethylformamide, N,N-dimethylacetamide and N-methylpyrrolidone, and sulfoxides such as dimethylsulfoxide and diethylsulfoxide. According to need, this solvent may be mixed with a hydrocarbon (e.g., xylene) that is compatible with the solvent. The reaction temperature of the step (b) is preferably not higher than 200° C., more preferably from 60 to 180° C., still more preferably from 80 to 150° C. The reaction time of the step (b) is suitably decided depending on the type of the metal fluoride of the step (b), and it may be up to 24 hr.

In case that a chlorohydrocarbon is fluorinated in a gas phase by hydrogen fluoride in the presence of catalyst, it is usual that these chlorohydrocarbon and hydrogen fluoride are previously vaporized by heating and then introduced into the reaction zone of this fluorination. This heating is usually conducted at a temperature close to the decomposition temperature of the raw material of this fluorination. In particular, a chlorohydrocarbon-having a larger number of chlorine atoms has a higher boiling point. Furthermore, it is known that hydrogen fluoride itself may act as a catalyst for polymerization or isomerization. Thus, the above heating for the vaporization may cause polymerization of the chlorohydrocarbon. As time passes, the resultant high boiling point compounds may turn into tarry substances or solid carbon. These undesirable substances may clog the reactor, and may cover the catalyst surface to reduce the catalyst activity. If the reaction temperature of the step (a) is lowered in order to prevent these problems, conversion may become too low.

In view of the above, according to the invention, it is preferable in the fluorination of the step (a) to provide a plurality of reaction zones arranged in series and make the reaction temperature of each reaction zone independently controllable. Each reaction zone may be an independent reactor. In other words, there may be provided a plurality of reactors for conducting the step (a). Alternatively, it is optional to provide only a single reactor having a heating device to independently control the temperature of each reaction zone of the reactor. In other words, this reactor has therein a plurality of reaction zones. The manner to conduct the step (a) is not particularly limited, and it may be one of the fixed bed method, the fluidized bed method and the moving bed method. Of these, the fixed bed method is the most preferable. The type of the reactor is not particularly limited, and it is preferable to use a single-tubular or multi-tubular type reactor having an outside heating system.

In the invention, the number of the reaction zones arranged in series is preferably at least two, and it is preferably not greater than 10 in view of economical viewpoint and the operational complexity. It is more preferably from two to four. Herein, the first reaction zone or reactor is defined as one into which the raw materials of the step (a) are introduced. The subsequent reaction zones or reactors until the last reaction zone or reactor are arranged in order. The respective temperatures of the reaction zones may independently be controlled depending on the raw materials, catalyst of each reaction zone, the reaction condition, the aimed reaction products. In fact, it is preferable to adjust the temperature of the last reaction zone, which is a main reaction zone to conduct the step (a), such that desirable conversion and selectivity can be obtained. Furthermore, it is preferable that the reaction zone temperatures of from the first to the last reaction zones are adjusted in ascending order. In other words, the reaction zone temperature increases stepwise from the first to the last reaction zones. The size of each reaction zone may arbitrarily be set. In fact, the main reaction zone is preferably larger than the first reaction zone in size in order to easily control the reaction of the step (a). The same or different catalysts may be introduced into the reaction zones, but it is preferable to use the same catalyst for all of the reaction zones. In the invention, the temperature of the main reaction zone has relation to the designed conversion, selectivity and catalyst lifetime and is preferably from 80 to 800° C. As stated above, the reaction temperature depends largely on the type of catalyst. If the aimed reaction product can be obtained at a reaction temperature lower than 80° C., it is not necessary to provide a plurality of reaction zones. If the reaction temperature is higher than 800° C., the reaction rate may become high. However, the catalyst lifetime may become too short, and it requires a large amount of heat energy.

In the invention, it is preferable to adjust the reaction temperature of the first reaction zone to be lower than boiling point of the second perhalogenated cyclopentene. In other words, an expected reaction, which should occur in the first reaction zone, does not necessarily require the reaction temperature that is not lower than the boiling point of the second perhalogenated cyclopentene under a pressure of the reaction system. At the reaction temperature lower than this boiling point, chlorine atoms of the second perhalogenated cyclopentene may partially be replaced with fluorine atoms in the first reaction zone. With this, the second perhalogenated cyclopentene may turn into a low boiling point intermediate. It is assumed that such partially fluorinated low-boiling-point intermediate is not easily polymerized, but effectively turns into an aimed reaction product in a subsequent reaction zone having a temperature higher than that of the first reaction zone. As a result, it may become possible to decrease the production of undesirable perfluorinated compounds and tarry substances, increase yield of the aimed reaction product, and prolong the fluorination catalyst in lifetime.

In case that the fluorination of the step (a) is conducted by providing a plurality of reaction zones, the molar ratio of the second perhalogenated cyclopentene (e.g., octachlorocyclopentene), which is supplied to the reaction zone, to hydrogen fluoride varies, depending on the temperature of the main or the last reaction zone. The molar ratio of the second perhalogenated cyclopentene to hydrogen fluoride is preferably from 1/60 to 1/6, more preferably from 1/50 to 1/8, still more preferably from 1/40 to 1/10. It is preferable to suitably reduce the amount of hydrogen fluoride relative to that of the second perhalogenated cyclopentene, in case that the second perhalogenated cyclopentene is in a partially fluorinated form or that the first perhalogenated cyclopentene is intended to have a lower degree of fluorination. If the amount of hydrogen fluoride is too small, conversion and yield may become too low. Even if it is excessive, it will be recovered and separated after the reaction and then reused as a raw material of the reaction. Thus, this does not cause any problems.

In the invention, it is preferable to introduce into the first reaction zone hydrogen fluoride in an amount that is larger than that for conducting the reaction of the first reaction zone. In fact, the temperature of the first reaction zone can be adjusted to a relatively low temperature by introducing a sufficient amount of hydrogen fluoride thereinto. This hydrogen fluoride may partly be replaced with an inert gas. However, it is preferable to omit this inert gas, unless the use of inert gas has other advantageous effects. With the omission of inert gas, separation and purification of the reaction product become easier. Thus, it is particularly preferable that inert gas is substantially not present in each reaction zone. It is preferable to introduce the total amount of hydrogen fluoride required for the step (a) into the first reaction zone in order to decrease the reaction temperature, although it is not necessarily needed.

In the invention, it is preferable that the second perhalogenated cyclopentene is preheated at a temperature that is about 1–50° C. lower than the boiling point of the second perhalogenated cyclopentene and that hydrogen fluoride is preheated at a temperature close to that of the first reaction zone. Although these compounds may be preheated simultaneously in a single vessel, it is preferable to preheat these compounds in different vessels.

In the invention, it is preferable from the viewpoint of reaction to remove hydrogen chloride that has been generated in one reaction zone, prior to the next reaction zone, since this hydrogen chloride is not a preferable substance in the next reaction of the next reaction zone in view of chemical equilibrium. However, the removal of hydrogen chloride often causes the removal of unreacted hydrogen fluoride at the same time. Thus, it is not necessarily-needed to remove such hydrogen chloride. On the other hand, in case that small amounts of high boiling point organic matters are produced in each reaction zone, it may be preferable to remove these organic matters therefrom in order to prolong the catalyst in lifetime. The method of this removal is not particularly limited. For example, they may be removed by adsorption on activated carbon, absorption by sulfuric acid or solvent, separation by cooling liquefaction.

In the invention, when octachlorocyclopentene is fluorinated by the step (a) by providing a plurality of reaction zones, there are obtained in the reaction zones intermediates or reaction products, such as octafluorocyclopentene, 1-chloro-2,3,3,4,4,5,5-heptafluorocyclopentene, 1,2-dichloro-3,3,4,4,5,5-hexafluorocyclopentene, trichloropentafluorocyclopentene, tetrachlorotetrafluorocyclopentene, pentachlorotrifluorocyclopentene, hexachlorodifluorocyclopentene, and heptachloromonofluorocyclopentene. In the invention, intermediates are not particularly limited as long as they are chlorofluorocyclopentenes.

The following nonlimitative catalyst preparations are illustrative of the present invention. Fluorination Catalysts C2–C21 were respectively prepared in the following Catalyst Preparations 2–21.

Catalyst Preparation 1

At first, 800 g of an activated alumina, KHS-46 (trade name) of SUMITOMO CHEMICAL CO., LTD. having a particle diameter of 4–6 mm, was washed with water to remove powder from its surface. Separately, 306 g of hydrogen fluoride (anhydrous hydrofluoric acid) was dissolved in 2,760 g of water, to prepare a 10% hydrogen fluoride aqueous solution. Then, this solution was gradually poured onto the activated alumina, followed by stirring. After that, it was allowed to stand still for 3 hr, and then the activated alumina was taken out of the solution, then washed with water, then filtered, and then dried for 2 hr in an electric furnace at 200° C. The dried activated alumina in an amount of 800 ml was introduced into a stainless steel (SUS 304) cylindrical reaction tube having an inside diameter of 4.2 cm and an axial length of 60 cm. The temperature of the reaction tube was increased to 200° C. in the furnace, while nitrogen was allowed to flow through the reaction tube. Then, hydrogen fluoride, together with nitrogen, was allowed to flow therethrough, to fluorinate the activated alumina. As this fluorination proceeded, the temperature increased. However, the flow rates of nitrogen and hydrogen fluoride were suitably adjusted to make the temperature not higher than 400° C. After the heat generation terminated, the temperature of the furnace was maintained at 400° C. for 2 hr, thereby to prepare a fluorinated alumina.

Catalyst Preparation 2

At first, a 1.3 liter $CrCl_3$ solution was prepared by dissolving 435 g of $CrCl_3.6H_2O$ into pure water, as shown in Table 1. Into this solution 200 g of the fluorinated alumina obtained in Catalyst Preparation 1 was immersed, as shown in Table 1, and the resultant solution was allowed to stand still for one day and one night. Then, the alumina was separated from the solution by filtration, and then was dried for one day and one night at 100° C. in a hot-air circulating type oven. The thus obtained chromium-carried alumina in an amount of 200 ml was put into a cylindrical reaction tube that is equipped with an electric furnace and is made of stainless steel (SUS304) and has a diameter of 2.5 cm and an axial length of 40 cm. The reaction tube temperature was increased to 300° C., while nitrogen gas was allowed to flow therethrough. Then, at the time when it was found that steam flow there from stopped, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the chromium-carried alumina reached the end of exit of the reaction tube, the reaction tube temperature was further increased to 400° C. Then, this condition was maintained for 1 hr, thereby preparing a fluorination catalyst C2.

TABLE 1

| Catalyst No. | Metal Compound Type | Weight (g) | Water for Dissolving Metal Compound | Carrier Type | Carrier Amount |
|---|---|---|---|---|---|
| C2 | $CrCl_3.6H_2O$ | 435 | 1.3 L*** | FA* | 200 g |
| C3 | $CrCl_3.6H_2O$ | 448 | 1.3 L*** | AC** | 200 g |
| C4 | $Cr(NO_3)_3.9H_2O$ | 495 | 1000 g | AC** | 200 g |
| C5 | $Cr(NO_3)_3.9H_2O$ | 495 | 1000 g | FA* | 200 g |
| C6 | $Cr(NO_3)_3.9H_2O$ | 3960 | 8000 g | AC** | 4200 g |
| C7 | $Cr_2O_3$ | — | — | — | — |
| C8 | $Cr(NO_3)_3.9H_2O$ | 6720 | 3280 g | AC** | 2000 g |
| C9 | $SbCl_5$ | 100 | — | AC** | 200 mL |
| C10 | $Fe(NO_3)_3.9H_2O$ | 202 | 221 g | AC** | 300 mL |
| C11 | $Zn(NO_3)_2.6H_2O$ | 251 | 149 g | AC** | 250 mL |
| C12 | $Fe(NO_3)_3.9H_2O$ | 101 | 604 g | AC** | 500 mL |
| C13 | $Fe(NO_3)_3.9H_2O$ | 202 | 221 g | FA* | 300 mL |
| C14 | $CoCl_2.6H_2O$ | 238 | 217 g | FA* | 300 mL |
| C15 | $Co(NO_3)_2.9H_2O$ | 291 | 349 g | AC** | 300 mL |
| C16 | $NiCl_2.6H_2O$ | 238 | 216 g | FA* | 300 mL |
| C17 | $Ni(NO_3)_2.9H_2O$ | 291 | 349 g | AC** | 300 mL |
| C18 | $Cu(NO_3)_2.3H_2O$ | 242 | 415 g | FA* | 300 mL |
| C19 | $Cu(NO_3)_2.3H_2O$ | 242 | 415 g | AC** | 300 mL |
| C20 | $MnCl_2.4H_2O$ | 198 | 243 g | FA* | 300 mL |
| C21 | $Al(NO_3)_3.9H_2O$ | 188 | 185 g | AC** | 300 mL |

*FA: Fluorinated Alumina,
**AC: Activated Carbon,
***The total amount of the metal compound solution was adjusted to 1.3 liter.

Catalyst Preparation 3

At first, a 1.3-liter $CrCl_3$ solution was prepared by dissolving 448 g of $CrCl_3.6H_2O$ into pure water, as shown in Table 1. In this solution 200 g of a granular coconut husk activated carbon made by Takeda Chemical Industries, Ltd. having a trade name of GRANULAR SHIRO SAGI GX made of columnar carbon grains having a size of 4–6 mesh screen was immersed for one day and one night. Then, the activated carbon was separated from the solution by filtration, and then put into an eggplant type flask for drying under vacuum at 70° C. using an evaporator. The thus obtained chromium-carried activated alumina in an amount of 200 ml was put into a cylindrical reaction tube that is equipped with an electric furnace and is made of stainless steel (SUS304) and has a diameter of 2.5 cm and an axial length of 40 cm. The reaction tube temperature was increased to 300° C., while nitrogen gas was allowed to flow therethrough. Then, at the time when it was found that steam flow therefrom stopped, it was started to allow hydrogen fluoride to flow therethrough, together with nitrogen gas. Then, hydrogen fluoride concentration of the mixture of hydrogen fluoride and nitrogen was gradually increased. The reaction tube temperature was further increased to 350° C. Then, this condition was maintained for 1 hr, thereby preparing a fluorination catalyst C3.

Catalyst Preparation 4

At first, 495 g of $Cr(NO_3)_3.9H_2O$ was dissolved into 1,000 g of pure water. In the resultant solution 200 g of a granular activated carbon, which is the same as that of Catalyst Preparation 3, was immersed for one day and one night. Then, the activated carbon was separated from the solution by filtration, and then put into an eggplant type flask for drying under vacuum at 70° C. using an evaporator. After the drying, the temperature was increased to 150° C. under atmospheric pressure to pyrolyze the nitrate. This heating was stopped at the time when the generation of $NO_2$ terminated. The obtained chromium-carried activated carbon in an amount of 200 ml was put into a cylindrical reaction tube, which is the same as that Catalyst Preparation 2. The reaction tube temperature was increased to 350° C., while nitrogen gas was allowed to flow therethrough. After that, it was decreased to 150° C. and then it was started to allow hydrogen fluoride to flow therethrough, together with nitrogen gas. Under this condition, the reaction tube temperature was increased again to 350° C. Then, this condition was maintained for 1 hr, thereby preparing a fluorination catalyst C4.

Catalyst Preparation 5

At first, 495 g of $Cr(NO_3)_3 \cdot 9H_2O$ was dissolved into 1,000 g of pure water. In the resultant solution 200 g of a fluorinated alumina, which is the same as that of Catalyst Preparation 1, was immersed for one day and one night. Then, the alumina was separated from the solution by filtration, and then put into an eggplant type flask for drying under vacuum at 70° C. using an evaporator. After the drying, the temperature was increased to 150° C. under atmospheric pressure to pyrolyze the nitrate. This heating was stopped at the time when the generation of $NO_2$ terminated. The obtained chromium-carried alumina in an amount of 200 ml was put into a cylindrical reaction tube, which is the same as that Catalyst Preparation 2. The reaction tube temperature was increased to 400° C., while nitrogen gas was allowed to flow therethrough. Then, at the time when it was found that steam flow therefrom stopped, the reaction tube temperature was decreased to 150° C., and then it was started to allow hydrogen fluoride to flow therethrough, together with nitrogen gas. Under this condition, the reaction tube temperature was increased again to 400° C. Then, this condition was maintained for 1 hr, thereby preparing a fluorination catalyst C5.

Catalyst Preparation 6

At first, 3,960 g of $Cr(NO_3)_3 \cdot 9H_2O$ was dissolved into 8,000 g of pure water. In the resultant solution 4,200 g of a granular activated carbon, which is the same as that of Catalyst Preparation 3, was immersed for one day and one night. Then, the activated carbon was separated from the solution by filtration, and then put into an eggplant type flask for drying under vacuum at 70° C. using an evaporator. After the drying, the temperature was increased to 150° C. under atmospheric pressure to pyrolyze the nitrate. This heating was stopped at the time when the generation of $NO_2$ terminated. The obtained chromium-carried activated carbon in an amount of 4,200 ml was put into a cylindrical reaction tube that is equipped with an electric furnace and is made of stainless steel (SUS304) and has a diameter of 5.4 cm and an axial length of 200 cm. The reaction tube temperature was increased to 350° C., while nitrogen gas was allowed to flow therethrough. After that, it was decreased to 150° C., and then it was started to allow hydrogen fluoride to flow therethrough, together with nitrogen gas. Under this condition, the reaction tube temperature was increased again to 350° C. Then, this condition was maintained for 1 hr, thereby preparing a fluorination catalyst C6.

Catalyst Preparation 7

At first, a granular $Cr_2O_3$ of Kojundo Kagaku Kenkyusho Co., which is made by power sintering and has a particle size not larger than 4-mesh screen, in an amount of 200 ml was put into a cylindrical reaction tube, which is the same as that Catalyst Preparation 2. The reaction tube temperature was increased to 350° C., while nitrogen gas was allowed to flow therethrough. After that, it was decreased to 150° C., and then it was started to allow hydrogen fluoride to flow therethrough, together with nitrogen gas. Under this condition, the reaction tube temperature was increased again to 350° C. Then, this condition was maintained for 1 hr, thereby preparing a fluorination catalyst C7.

Catalyst Preparation 8

At first, 6.72 kg of $Cr(NO_3)_3 \cdot 9H_2O$ was dissolved into 3.28 kg of pure water. In the resultant solution 2.00 kg of a granular activated carbon, which is the same as that of Catalyst Preparation 3, was immersed for one day and one night. Then, the activated carbon was separated from the solution by filtration, and then put into an eggplant type flask for drying under vacuum at 70° C. using an evaporator. After the drying, the temperature was increased to 150° C. under atmospheric pressure to pyrolyze the nitrate. This heating was stopped at the time when the generation of $NO_2$ terminated, thereby preparing a fluorination catalyst C8.

Catalyst Preparation 9

At first, a granular activated carbon, which is the same as that of Catalyst Preparation 3, was dried under vacuum at 100–120° C. Then, 200 ml of this activated carbon was put into a 300 ml eggplant type flask. Then, 100 g of antimony pentachloride was dropped into the flask at a temperature not higher than 50° C., while the flask was well stirred. Then, 200 ml of the obtained catalyst was put into a cylindrical reaction tube, which is the same as that of Catalyst Preparation 2. Then, the reaction tube temperature was increased from room temperature to 150° C. and then maintained at 150° for 1 hr, while nitrogen was introduced at a rate of 1.2 liter per hr into the reaction tube, and at the same time hydrogen fluoride, which has been gasified by a gasifier provided at an upper portion of the reaction tube, was introduced at a rate of 36 g per hr into the reaction tube. Then, the introduction of hydrogen fluoride was stopped, and the reaction tube was cooled down to room temperature. After that, while chlorine was introduced at a rate of 300 ml per hr into the reaction tube, the reaction tube temperature was increased from room temperature to 150° C. Then, this condition was maintained for 1 hr, thereby preparing a fluorination catalyst C9.

Catalyst Preparations 10, 11, 12, 15, 17, 19 and 21

In these Catalyst Preparations, Catalyst Preparation 4 was repeated except in that the type and the amount of the metal compound, the amount of water to dissolve therein the metal compound, the amount of the activated carbon of Catalyst Preparation 3 were modified as shown in Table 1. With this, fluorination catalysts C10, C11, C12, C15, C17, C19 and C21 were prepared.

Catalyst Preparation 13 and 18

In these Catalyst Preparations, Catalyst Preparation 5 was repeated except in that the type and the amount of the metal compound, the amount of water to dissolve therein the metal compound, the amount of the fluorinated alumina of Catalyst Preparation 1 were modified as shown in Table 1. With this, fluorination catalysts C13 and C18 were prepared.

Catalyst Preparations 14, 16 and 20

In these Catalyst Preparations, Catalyst Preparation 3 was repeated except in that the type and the amount of the metal compound, the amount of water to dissolve therein the metal compound, the amount of the fluorinated alumina of Catalyst Preparation 1 were modified as shown in Table 1. With this, fluorination catalysts C14, C16 and C20 were prepared.

The following nonlimitative examples are illustrative of the present invention.

EXAMPLE 1

At first, 190 ml of the gas phase fluorination catalyst prepared at Catalyst Preparation 2 was put in a cylindrical reaction tube that is equipped with an electric furnace and is made of stainless steel (SUS304) and has a diameter of 2.5 cm and an axial length of 40 cm. Then, while nitrogen gas was allowed to flow therethrough at a rate of about 1.2 liter/hr, the reaction tube temperature was increased to 300° C. Then, hydrogen fluoride was allowed therethrough at a rate of 12 g/hr together with nitrogen gas. Then, the reaction tube temperature was further increased. When it reached 330° C., the nitrogen gas flow was stopped. Then, as shown in Table 2, it was started to allow hydrogen fluoride and octachlorocyclopentene to flow therethrough at rates of 12 g/hr and 18 g/hr, respectively. In this manner, 90 g of octachlorocyclopentene in total was supplied to the reaction tube, and a gas component generated in the reaction tube was collected by a trap having iced water. With this, 62 g of an organic matter was collected. With an analysis by gas chromatography, as shown in Table 3 it was found that this organic matter contains 27.3% of 1,2-dichloro-3,3,4,4,5,5-hexafluorocyclopentene, 40.7% of trichloropentafluorocyclopentene, 22.7% of tetrachlorotetrafluorocyclopentene, and 3.9% of pentachlorotrifluorocyclopentene. These percentages are areal percentages in chromatogram, and FID was used as detector of gas chromatography.

TABLE 2

| Catalyst | Reaction Temp. (° C.) | Reaction Time (hr) | 8C-CPE* Flow Rate (g/hr) | HF Flow Rate (g/hr) |
|---|---|---|---|---|
| Ex. 1 | C2 | 330 | 5 | 18 | 12 |
| Ex. 2 | C2 | 330 | 5 | 18 | 30 |
| Ex. 3 | C3 | 330 | 5 | 18 | 12 |
| Ex. 4 | C4 | 330 | 13 | 18 | 16 |
| Ex. 5 | C5 | 330 | 5 | 18 | 30 |
| Ex. 6 | C7 | 330 | 3 | 18 | 23 |
| Ex. 7 | C10 | 330 | 5 | 21.0 | 35.4 |
| Ex. 8 | C9 | 200 | 3.5 | 26.7 | 41.2 |
| Ex. 9 | C9 | 175 | 3.5 | 28.3 | 44.0 |
| Ex. 10 | C9 | 175 | 3.0 | 24.1 | 41.1 |

*8C-CPE: octachlorocyclopentene.

TABLE 3

| | Collected Organic Matter (g) | Collected Organic Matter Composition (areal %) | | | | |
|---|---|---|---|---|---|---|
| | | 1C7F-CPE | 2C6F-CPE* | 3C5F-CPE* | 4C4F-CPE* | 5C3F-CPE* |
| Ex. 1 | 62 | 0.2 | 27.3 | 40.7 | 22.7 | 3.9 |
| Ex. 2 | 60 | 0.5 | 53.2 | 33.1 | 7.4 | 1.9 |
| Ex. 3 | 60 | 0.5 | 57.0 | 24.9 | 15.3 | 1.3 |
| Ex. 4 | 159 | 0.7 | 73.6 | 20.2 | 4.9 | 0.3 |
| Ex. 5 | 55 | 0.2 | 34.4 | 45.2 | 12.1 | 1.0 |
| Ex. 6 | 37 | — | 9.0 | 60.1 | 23.1 | 2.5 |
| Ex. 7 | 65.4 | 0.5 | 17.8 | 71.4 | 9.2 | 0.1 |
| Ex. 8 | 58.0 | — | 75.7 | 18.1 | 4.9 | 0.4 |
| Ex. 9 | 56.6 | — | 77.4 | 16.4 | 4.8 | 0.2 |
| Ex. 10** | 42.2 | — | 63.4 | 24.5 | 9.5 | 1.3 |

*1C7F-CPE: 1-chloro-2,3,3,4,4,5,5-heptafluorocyclopentene; 2C6F-CPE: 1,2-dichloro-3,,3,4,4,5,5-hexafluorocyclopentene; 3C5F-CPE: trichloropentafluorocyclopentene; 4C4F-CPE: tetrachlorotetrafluorocyclopentene; and 5C3F-CPE: pentachlorotrifluorocyclopentene.
**The collected organic matter composition of Example 10 further contained 0.5% of hexachlorodifluorocyclopentene and 0.2% of heptachlorofluorocyclopentene.

EXAMPLES 2–7

In these examples, Example 1 was repeated except in that the type of the fluorination catalyst, the reaction time, and the flow rates of octachlorocyclopentene and hydrogen fluoride were modified as shown in Table 2. The results are shown in Table 3.

EXAMPLE 8

At first, 200 ml of the activated carbon of Catalyst Preparation 9 was put in a cylindrical reaction tube that is the same as that of Example 1. Then, while nitrogen and hydrogen fluoride were allowed to flow therethrough at 50° C. at respective rates of 1.2 liter/hr and 41.2 g/hr, 93.3 g of octachlorocyclopentene and 144.3 g of hydrogen fluoride were supplied to the reaction tube by spending 3.5 hr. A gas component generated in the reaction tube was collected by a trap having iced water. The obtained organic matter was analyzed in the same manner as that of Example 1. The results are shown in Table 3.

EXAMPLE 9

At first, 100 ml of the activated carbon of Catalyst Preparation 9 was put in a cylindrical reaction tube that is the same as that of Example 1. Then, while nitrogen, chlorine and hydrogen fluoride were allowed to flow therethrough at 50° C. at respective rates of 1.2 liter/hr, about 150 ml/hr and 44 g/hr, the reaction tube temperature was increased to 175° C. At this time, the flow of nitrogen was stopped, and then 99.1 g of octachlorocyclopentene and 153.9 g of hydrogen fluoride were supplied to the reaction tube by spending 3.5 hr. A gas component generated in the reaction tube was collected by a trap having iced water. The obtained organic matter was analyzed in the same manner as that of Example 1. The results are shown in Table 3.

EXAMPLE 10

In this example, Example 9 was repeated except in that reaction conditions were modified as shown in Table 2. The results are shown in Table 3.

EXAMPLE 11

At first, 190 ml of the fluorinated alumina of Catalyst Preparation 5 was put in a cylindrical reaction tube that is the same as that of Example 1. Then, while nitrogen was allowed to flow therethrough at a rate of about 1.2 liter/hr, the reaction tube temperature was increased to 300° C. Then, it was started to allow hydrogen fluoride to flow therethrough at a rate of 12 g/hr, together with nitrogen. The reaction tube temperature was further increased to 450° C., and at this time the flow of nitrogen was stopped. Then, it was started to supply hydrogen fluoride and 1,2-dichloro-3,3,4,4,5,5-hexafluorocyclopentene (2C6F-CPE) to the reaction tube at respective rates of 12 g/hr and 15 g/hr, as shown in Table 4. In total, 75 g of 2C6F-CPE was supplied thereto, and a gas component generated in the reaction tube was collected by a trap having iced water. The obtained organic matter was analyzed in the same manner as that of Example 1. The results are shown in Table 5.

TABLE 4

| | Catalyst | Reaction Temp. (° C.) | Reaction Time (hr) | 2C6F-CPE* Flow Rate (g/hr) | HF Flow Rate (g/hr) |
|---|---|---|---|---|---|
| Ex. 11 | C5 | 450 | 5 | 15 | 12 |
| Ex. 12 | C5 | 500 | 5 | 15 | 12 |
| Ex. 13 | C4 | 330 | 3 | 21.6 | 43.2 |
| Ex. 14 | C10 | 330 | 3 | 30.0 | 34.2 |
| Ex. 15 | C12 | 330 | 3 | 22.8 | 27.0 |
| Ex. 16 | C14 | 450 | 3 | 21.6 | 21.0 |
| Ex. 17 | C15 | 330 | 4 | 24.0 | 26.4 |
| Ex. 18 | C16 | 450 | 3 | 16.2 | 21.6 |

TABLE 4-continued

|  | Catalyst | Reaction Temp. (° C.) | Reaction Time (hr) | 2C6F-CPE* Flow Rate (g/hr) | HF Flow Rate (g/hr) |
| --- | --- | --- | --- | --- | --- |
| Ex. 19 | C17 | 330 | 2 | 24.6 | 22.2 |
| Ex. 20 | C19 | 330 | 2 | 24.0 | 26.4 |
| Ex. 21 | C21 | 330 | 3 | 21.6 | 24.0 |
| Ex. 22 | C11 | 330 | 2 | 24.0 | 22.8 |
| Ex. 23 | C13 | 450 | 2 | 19.2 | 19.2 |
| Ex. 24 | C18 | 470 | 2 | 23.4 | 22.2 |
| Ex. 25 | C20 | 330 | 3 | 27.0 | 28.8 |

*2C6F-CPE: 1,2-dichloro-3,3,4,4,5,5-hexafluorocyclopentene.

TABLE 5

|  | Collected Organic Matter (g) | Collected Organic Matter Composition (area %) | | | |
| --- | --- | --- | --- | --- | --- |
|  |  | 8F-CPE* | 1C7F-CPE* | 2C6F-CPE* | 3C5F-CPE* |
| Ex. 11 | 63 | 0.2 | 26.8 | 64.6 | 2.7 |
| Ex. 12 | 53 | 0.3 | 21.2 | 59.7 | 3.8 |
| Ex. 13 | 49.6 | 0.6 | 23.5 | 74.3 | 0.8 |
| Ex. 14 | 70.2 | 0.3 | 21.1 | 78.2 | 0.1 |
| Ex. 15 | 52.0 | 0.6 | 26.7 | 73.2 | 0.1 |
| Ex. 16 | 56.2 | 0.3 | 17.7 | 79.2 | 1.2 |
| Ex. 17 | 80.3 | 1.2 | 16.1 | 81.1 | 0.9 |
| Ex. 18 | 39.8 | 1.0 | 26.2 | 68.3 | 1.7 |
| Ex. 19 | 35.4 | 1.2 | 24.2 | 70.1 | 0.2 |
| Ex. 20 | 39.4 | — | 11.2 | 86.5 | 0.2 |
| Ex. 21 | 53.7 | 0.4 | 21.3 | 77.1 | 0.2 |
| Ex. 22 | 39.6 | 0.5 | 24.2 | 74.0 | 0.1 |
| Ex. 23 | 25.4 | 0.2 | 14.2 | 82.0 | 1.3 |
| Ex. 24 | 39.8 | — | 9.7 | 88.9 | 0.6 |
| Ex. 25 | 76.5 | — | 1.2 | 97.9 | 0.3 |

*8F-CPE: octafluorocyclopentene; 1C7F-CPE: 1-chloro-2,3,3,4,4,5,5-heptafluorocyclopentene; 2C6F-CPE: 1,2-dichloro-3,,3,4,4,5,5-hexafluorocyclopentene; and 3C5F-CPE: trichloropentafluorocyclopentene.

EXAMPLES 12–25

In these examples, Example 11 was repeated except in that reaction conditions were modified as shown in Table 4. The results are shown in Table 5.

EXAMPLE 26

At first, a 300 ml reactor was charged with 59.5 g of dried potassium fluoride and 114 g of N,N-dimethylformamide, followed by heating at 130° C. Then, 100 g of the reaction products of Example 4, which had been well dried, that is, a perhalogenated cyclopentene mixture having a composition shown in Table 3, was added drop wise to the reactor by spending 4.9 hr, and at the same time an organic matter generated in the reactor was distilled off at a temperature of 27–28° C., thereby to obtain 76.3 g of octafluorocyclopentene (yield: 90%).

EXAMPLE 27

In this example, there was a fluorination reactor having first and second reactors that are connected with each other in series by piping. The first and second reactors were respectively charged with the activated carbon (gas phase fluorination catalyst) of Catalyst Preparation 8 in amounts of 400 ml and 2.0 liter. The first reactor was a stainless steel (SUS304) cylindrical reaction tube that is heatable by an electric heater and has a diameter of 4.2 cm and an axial length of 40 cm. The second reactor was a jacket-type cylindrical reaction tube that is heatable by a heat medium and made of a stainless steel (SUS304) and has a diameter of 5.4 cm and an axial length of 100 cm.

A preliminary arrangement of the first reactor for stabilizing the catalyst therein was conducted as follows. While nitrogen gas was allowed to flow through the first reactor at a rate of about 12 liter/hr, the first reactor temperature was increased to 350° C. Then, the first reactor temperature was decreased to 150° C. After that, it was started to allow hydrogen fluoride to flow therethrough together with nitrogen gas. While the hydrogen fluoride concentration was gradually increased, the first reactor temperature was increased to 330° C. At this time, the flow of nitrogen gas was stopped. Then, the first reactor temperature was decreased to 250° C. Then, hydrogen fluoride, which had been heated to 250° C. by passing through a preheating device, was supplied to the first reactor at a rate of 330 g/hr.

A preliminary arrangement of the second reactor for stabilizing the catalyst therein was conducted as follows. While nitrogen gas was allowed to flow through the second reactor at a rate of about 12 liter/hr, the second reactor temperature was increased to 350° C. Then, the second reactor temperature was decreased to 150° C. After that, it was started to allow hydrogen fluoride to flow therethrough together with nitrogen gas. While the hydrogen fluoride concentration was gradually increased, the second reactor temperature was increased to 330° C. At this time, the flow of nitrogen gas was stopped. Then, hydrogen fluoride discharging from the first reactor was allowed to flow through the second reactor.

Then, octachlorocyclopentene, which had been preheated at 250° C., was supplied in the form of liquid to the first reactor at a rate of 210 g/hr. After the reaction was started, a generated gas component was sampled at an exit of the first reactor. Then, an acid gas (hydrogen fluoride and hydrogen chloride) was removed from the gas component, and the resultant gas component was analyzed with gas chromatography. With this, it was found that this gas component has a composition of 2.3% 1,2-dichloro-3,3,4,4,5,5-hexafluorocyclopentene, 14.3% trichloropentafluorocyclopentene, 39.9% tetrachlorotetrafluorocyclopentene, 32.7% pentachlorotrifluorocyclopentene, 8.0% hexachlorodifluorocyclopentene, and 0.8% heptachloromonofluorocyclopentene.

The reaction was continued in the same manner as above. Thus, 42 kg of octachlorocyclopentene was supplied in total to the first reactor at a rate of 210 g/hr by spending 200 hr, and a generated gas discharging from the second reactor was collected by a trap having iced water. With this, 26.4 kg of an organic matter was obtained. This organic matter was analyzed by gas chromatography and found to have a composition of 2.0% 1-chloro-2,3,3,4,4,5,5-heptafluorocyclopentene, 77.0% 1,2-dichloro-3,3,4,4,5,5-hexafluorocyclopentene, 16.3% trichloropentafluorocyclopentene, 3.7% tetrachlorotetrafluorocyclopentene, and 0.3% pentachlorotrifluorocyclopentene.

After the reaction, the conditions of the preheating devices for octachlorocyclopentene and hydrogen fluoride and the condition of the catalyst in the vicinity of the inlet of the first reactor were observed with naked eyes. With this, organic matter, tarry substances and carbon residue were not found at all.

EXAMPLE 28

At first, a stainless steel (SUS304) cylindrical reaction tube, which is equipped with an electric furnace and has a diameter of 5.4 cm and an axial length of 200 cm, was charged with 4.2 liter of the activated carbon of Catalyst Preparation 6. Then, while nitrogen gas was allowed to flow through the reaction tube at a rate of about 30 liter/hr, the reaction tube temperature was increased to 300° C. Then, hydrogen fluoride was allowed to flow therethrough at a rate of 501 g/hr together with nitrogen gas. The reaction tube temperature was further increased to 330° C., and at this time the flow of nitrogen gas was stopped. Then, it was started to allow octachlorocyclopentene to flow therethrough at a rate of 305 g/hr, while hydrogen fluoride was allowed to flow therethrough at a rate of 501 g/hr. In this manner, 82.35 kg of octachlorocyclopentene was supplied to the reaction tube by spending 270 hr, and a generated gas discharging from the reaction tube was collected by a stainless steel (SUS316) receiver that was previously cooled down to 15° C. The collected reaction products (hydrogen fluoride and an organic matter) were separated into organic and aqueous layers. The separated organic layer was washed with a 10% sodium hydrogencarbonate aqueous solution and then dried with anhydrous calcium chloride. With this, 51.53 kg of an organic matter was obtained. By an analysis with gas chromatography, this organic matter was found to have a composition of 1.37% 1-chloro-2,3,3,4,4,5,5-heptafluorocyclopentene, 77.6% 1,2-dichloro-3,3,4,4,5,5-hexafluorocyclopentene, 16.5% trichloropentafluorocyclopentene, 3.6% tetrachlorotetrafluorocyclopentene, and 0.3% pentachlorotrifluorocyclopentene.

After the reaction, the conditions of preheating devices for octachlorocyclopentene and hydrogen fluoride and the condition of the catalyst in the vicinity of the inlet of the reaction tube were observed with naked eyes. With this, a considerable amount of carbon residue was found in the preheating device of octachlorocyclopentene. Thus, it is assumed that the decomposition of octachlorocyclopentene occurred. Furthermore, carbon residue was also found on the catalyst in the vicinity of the inlet of the reaction tube.

The entire disclosure of each of Japanese Patent Application Nos. 9-252222 filed on Sep. 17, 1997 and 10-194140 filed on Jul. 9, 1998, including specification, claims, and summary, is incorporated herein by reference in its entirety.

What is claimed is:

1. A method for producing 1,2-dichloro-3,3,4,4,5,5-hexafluorocyclopentene, said method comprising a step of:
    (a) fluorinating octachlorocyclopentene by hydrogen fluoride in a gas phase in the presence of a fluorination catalyst, said fluorination catalyst comprising at least one compound selected from the group consisting of $CrCl_3.6H_2O$, $Cr(NO_3)_3.9H_2O$, $Cr_2O_3$, $SbCl_5$, $Fe(NO_3)_3.9H_2O$, $Zn(NO_3)_2.6H_2O$, $CoCl_2.6H_2O$, $Co(NO_3)_2.9H_2O$, $NiCl_2.6H_2O$, $Ni(NO_3)_2.9H_2O$, $Cu(NO_3)_2.3H_2O$, $MnCl_2.4HO$, and $Al(NO_3)_3.9H_2O$.

2. A method according to claim 1, wherein said fluorination catalyst is carried on a carrier selected from the group consisting of activated carbon, alumina, partially fluorinated alumina, fluorinated alumina, and fluorinated aluminum.

3. A method according to claim 1, wherein the step (a) is conducted under conditions that said hydrogen fluoride is in an amount of from 6 to 60 moles per mol of said second perhalogenated cyclopentene, that a reaction temperature is from 150 to 800° C., that a contact time is from 0.1 to 300 seconds and that a reaction pressure is from 1 to 10 kg/cm².

4. A method according to claim 1, wherein the step (a) is conducted by a multistep reaction wherein there are provided "m" of reaction zones in number where m is an integer of from 2 to 10, said reaction zones being arranged in series and such that a reaction temperature of each reaction zone is independently controllable.

5. A method according to claim 1, wherein the step (a) is conducted by a multiple reaction wherein there are provided at least first and second reaction zones that are arranged in series, said first reaction zone preceding said second reaction zone in position, a reaction temperature of said first reaction zone being lower than a boiling point of said octachlorocyclopentene under an operating pressure of a reaction system of said first reaction zone.

6. A method according to claim 5, wherein a reaction product formed in said first reaction zone, together with at least one of hydrogen chloride formed in said first reaction zone and said hydrogen fluoride remaining unreacted in said first reaction zone after a reaction of said octachlorocyclopentene with said hydrogen fluoride in said first reaction zone, is transferred to said second reaction zone.

7. A method according to claim 5, wherein, prior to an introduction of said octachlorocyclopentene into said first reaction zone, said octachlorocyclopentene is preheated at a temperature that is lower than said boiling point of said octachlorocyclopentene under an operating pressure of a reaction system.

8. A method for producing octafluorocyclopentene, said method comprising:
    (a) fluorinating octachlorocyclopentene by hydrogen fluoride in a gas phase in the presence of a fluorination catalyst, said fluorination catalyst comprising at least one compound selected from the group consisting of $CrCl_3.6H_2O$, $Cr(NO_3)_3.9H_2O$, $Cr_2O_3$, $SbCl_5$, $Fe(NO_3)_3.9H_2O$, $Zn(NO_3)_2.6H_2O$, $CoCl_2.6H_2O$, $Co(NO_3)_2.9H_2O$, $NiCl_2.6H_2O$, $Ni(NO_3)_2.9H_2O$, $Cu(NO_3)_2.3H_2O$, $MnCl_2.4H_2O$, and $Al(NO_3)_3.9H_2O$; and
    (b) fluorinating a reaction product of step (a) in a way that is different from that of step (a) into said octafluorocyclopentene.

9. A method according to claim 8, wherein said reaction product of the step (a) comprises 1,2-dichloro-3,3,4,4,5,5-hexafluorocyclopentene.

10. A method according to claim 8, wherein said fluorination catalyst is carried on a carrier selected from the group consisting of activated carbon, alumina, partially fluorinated alumina, fluorinated alumina, and fluorinated aluminum.

11. A method according to claim 8, wherein said reaction product of step (a) is fluorinated in step (b) by a metal fluoride, thereby to exchange chlorine atom of said reaction product of step (a) for fluorine atom of said metal fluoride.

12. A method according to claim 11, wherein said metal fluoride is selected from the group consisting of lithium fluoride, sodium fluoride, potassium fluoride, cesium fluoride, and rubidium fluoride.

* * * * *